United States Patent [19]

Buchel et al.

[11] 3,974,174
[45] Aug. 10, 1976

[54] 1-(1,2,4-TRIAZOLYL-1')-2-PHENOXY-4,4-DIMETHYL-PENTAN-3-ONES

[75] Inventors: Karl Heinz Buchel; Wolfgang Kramer, both of Wuppertal; Paul-Ernst Frohberger, Leverkusen, all of Germany

[73] Assignee: Bayer Aktiengesellschaft, Leverkusen, Germany

[22] Filed: June 27, 1974

[21] Appl. No.: 483,758

[30] Foreign Application Priority Data
July 10, 1973 Germany............................ 2335020

[52] U.S. Cl.............................. 260/308 R; 424/269
[51] Int. Cl.².................................... C07D 249/08
[58] Field of Search .............................. 260/308 R Primary Examiner—R. J. Gallagher
Attorney, Agent, or Firm—Burgess, Dinklage & Sprung

[57] ABSTRACT 1-(1,2,4-triazolyl-1')-2-phenoxy-4,4-dimethyl-pentan-3-ones of the formula

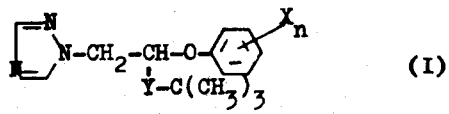

in which
n is an integer from 0 to 5,
X is halogen, halogenoalkyl, alkyl, alkoxy, alkylthio, alkylsulfonyl, nitro, nitrile, carbalkoxy or phenyl, and
Y is a keto group or a functional derivative of a keto group,
or a salt thereof,
which possess fungicidal properties.

6 Claims, No Drawings

1-(1,2,4-TRIAZOLYL-1')-2-PHENOXY-4,4-DIMETHYL-PENTAN-3-ONES

The present invention relates to and has for its objects the provision of particular new 1-(1,2,4-triazolyl-1')-2-phenoxy-4,4-dimethyl-pentan-3-ones optionally substituted on the phenyl ring and/or a functional derivative of the ketone group, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed in German Published Specification DOS NO. 1,795,249 that trityltriazoles, such as triphenyl-1,2,4-triazolyl-(1)-methane (Compound A) display fungicidal activity. However, their action is not always entirely satisfactory, especially when they are used in low amounts and low concentrations for combating fungal diseases of cereals. It is also disclosed in Phytophathology, Vol. 33, (1963) 1113, that zinc ethylene-1,2-bis-dithiocarbamate (Compound B) is effective for combating fungal diseases of plants. However, there are limitations on its use as a seed dressing since its activity is slight if low amounts and low concentrations are used.

The present invention provides, as new compounds, the 1-ethyl-triazoles of the general formula

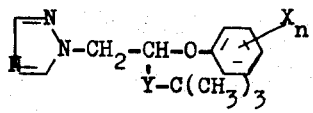 (I)

in which
n is an integer from 0 to 5,
X is halogen, halogenoalkyl, alkyl, alkoxy, alkylthio, alkylsulfonyl, nitro, nitrile, carbalkoxy or phenyl, and
Y is a keto group or a functional derivative of a keto group,
or a salt thereof.

ethylene-1,2-bis-dithiocarbamate, which are the closest active compounds. The compounds according to the present invention thus represent an enrichment of the art.

Preferably X is halogen such as fluorine, chlorine or bromine; halogenoalkyl with 1 or 2 carbon atoms and 2 to 5 halogen atoms, especially chlorine or fluorine atoms, such as trifluoromethyl; straight-chain or branched alkyl with 1 to 4 carbon atoms such as methyl, ethyl, n- or isopropyl or tert.-butyl; alkoxy or alkylthio with 1 to 4 carbon atoms such as methoxy, ethoxy, methylthio or ethylthio; alkyl-sulfonyl with 1 to 4 carbon atoms such as methylsulfonyl or ethylsulfonyl; nitro; nitrile; carbalkoxy with 1 to 4 carbon atoms in the alkyl radical or phenyl; n is 0, 1, 2 or 3; and Y is a keto group or a functional derivative of a keto group selected from oxime, hydrazone and ketal groups of the formula —C(OR)$_2$— wherein R is hydrogen or an alkyl radical preferably with 1 to 4 carbon atoms such as methyl or ethyl.

The present invention also provides a process for the preparation of a 1-ethyl-triazole of the formula (I), or a salt thereof, in which a compound of the general formula

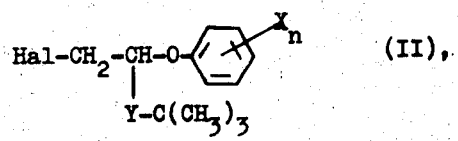 (II), in which
X, Y and n have the above-mentioned meanings, and
Hal is halogen, especially chlorine or bromine,
is reacted with 1,2,4-triazole, if appropriate in the presence of an acid-binding agent and in the presence of a polar solvent, the 1-ethyl-triazole so formed being converted, if required, into a physiologically tolerated salt thereof.

The halogen Hal in formula (II) is preferably chlorine or bromine, especially chlorine.

If 1-chloro-4,4-dimethyl-2-phenoxy-pentan-3-one and 1,2,4-triazole are used as starting compounds, the course of the reaction can be represented by the following equation:

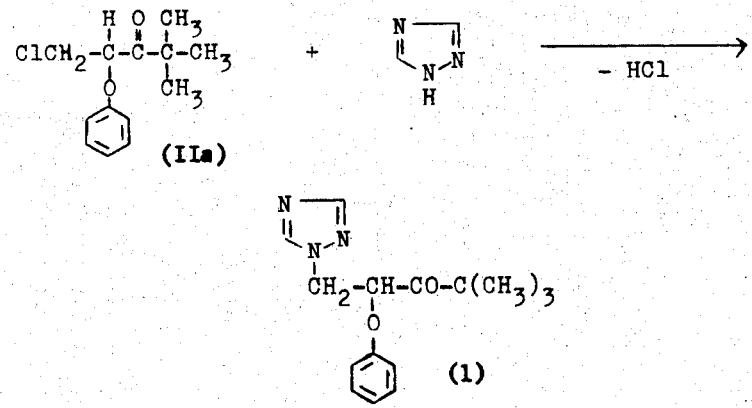

Surprisingly, the 1-ethyl-triazoles according to the present invention display a substantially greater fungicidal activity in fungal diseases of cereals than the trityl-triazoles, for example tris-phenyl-1,2,4-triazolyl-(1)-methane, known from the state of the art, and zinc The compounds of the formula (II) which can be used according to the invention have not previously been described in the literature. Such a compound can be prepared by reacting an ether-ketone of the general formula

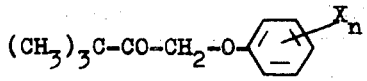

(III), in which

X and n have the above-mentioned meanings, with formaldehyde or a formaldehyde donor in the presence of alkali in an inert organic solvent, for example ethanol, at an elevated temperature, for example at the boil, and treating the resulting hydroxymethyl compound of the general formula

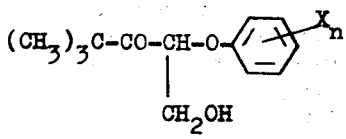

(IV), in which

X and n have the above-mentioned meanings, with a halogenating agent, for example thionyl chloride, in an inert polar organic solvent, for example methylene chloride, at room temperature. Isolation of the compound of the formula (II) and, if appropriate, conversion of its keto group into a functional derivative, is carried out in accordance with customary methods as is illustrated in Example 3 hereinbelow.

Ether-ketones of the formula (III) are known from patent application Ser. No. 318,963, filed Dec. 27, 1972, now pending, patent application Ser. No. 396,202, filed Sept. 11, 1973, now pending, and U.S. Pat. No. 3,812,142, the disclosures of which are incorporated herein by reference, or can be prepared according to processes described therein.

The following may be mentioned as examples of compounds of the formula (II) which can be used according to the present invention: 2-(4-chlorophenoxy)-1-chloro-4,4-dimethyl-pentan-3-one, 2-(4-fluorophenoxy)-1-chloro-4,4-dimethyl-pentan-3-one, 2-(4-bromophenoxy)-1-chloro-4,4-dimethyl-pentan-3-one, 2-phenoxy-1-chloro-4,4-dimethyl-pentan-3-one, 2-(2-diphenoxy)-1-chloro-4,4-dimethyl-pentan-3-one, 2-(4-diphenoxy)-1-chloro-4,4-dimethyl-pentan-3-one, 2-(2-methylphenoxy)-1-chloro-4,4-dimethyl-pentan-3-one, 2-(2,3-dimethylphenoxy)-1chloro-4,4-dimethyl-pentan-3-one, 2-(3,4-dimethylphenoxy)-1-chloro-4,4-dimethyl-pentan-3-one, 2-(2,4-dimethylphenoxy)-1-chloro-4,4-dimethyl-pentan-3-one, 2-(2,5-dimethylphenoxy)-1-chloro-4,4-dimethyl-pentan-3-one, 2-(2,6-dimethylphenoxy)-1-chloro-4,4-dimethyl-pentan-3-one, 2-(3,4,5-trichlorophenoxy)-1-chloro-4,4-dimethyl-pentan-3-one, 2-(3-trifluoromethylphenoxy)-1-chloro-4,4-dimethyl-pentan-3-one, 2-(4-trifluoromethylphenoxy)-1-chloro-4,4-dimethyl-pentan-3-one, 2-(2-trifluoromethylphenoxy)-1-chloro-4,4-dimethyl-pentan-3one and 2-(4-tertiary butylphenoxy)-1-chloro-4,4-dimethyl-pentan-3-one.

Diluents which can be used for the reaction according to the present invention are polar organic solvents. These include, for example, chlorinated hydrocarbons, such as methylene chloride, chloroform and chlorobenzene; ethers, such as diethyl ether, dioxane and tetrahydrofuran; ketones, such as acetone or ethyl methyl ketone; nitriles, such as acetonitrile; and formamides such as dimethylformamide.

All customary acid-binding agents can be used as acid-binders, especially alkali metal carbonates, alkaline earth metal carbonates and tertiary organic bases. The following may be mentioned as being particularly suitable; potassium carbonate, sodium carbonate, calcium carbonate, magnesium carbonate, barium carbonate, triethylamine and pyridine. An excess of the 1,2,4-triazole can also be employed as the acid-binding agent.

The reaction temperatures can be varied over a fairly wide range. In general, the reaction is carried out at between 50° and 150°C and preferably at between 80° and 120°C.

In general, the reaction is carried out under normal pressure.

In carrying out the process according to the invention, about 1 to 2.1 moles of 1,2,4-triazole or 1 mole of 1,2,4-triazole and 1 to 1.5 moles of acid-binder are preferably employed per mole of the compound of the formula (II).

To isolate the compound of the formula (I), the precipitate is filtered off and rinsed with solvent and the filtrate is freed from the solvent in vacuo. The resulting residue is taken up in an organic solvent and extracted by shaking with water to remove excess triazole. The organic phase is dried over sodium sulfate and freed from the solvent in vacuo. The oily residue in most cases crystallizes on trituration and can be purified further by recrystallization or by distillation if appropriate.

The compounds of the formula (I) can be used as their salts with physiologically tolerated acids. These include, in particular, the hydrogen halide acids, for example hydrobromic acid and, especially, hydrochloric acid, phosphoric acid, monofunctional and bifunctional carboxylic acids and hydroxycarboxylic acids, for example acetic acid, maleic acid, succinic acid, fumaric acid, tartaric acid, citric acid, salicylic acid, sorbic acid and lactic acid, and 1,5-naphthalene-disulfonic acid.

The active compounds according to the present invention display a strong fungitoxic action. They do not harm crop plants in the concentrations required to combat fungi and have a low toxicity towards warm-blooded animals. For these reasons, they are suitable for use as plant-protection agents for combating fungi. Fungitoxic agents are employed in plant protection for combating Archimycetes, Phycomycetes, Ascomycetes, Basidiomycetes and Fungi Imperfecti.

The active compounds according to the invention have a very broad spectrum of action and can be employed against parasitic fungi which attack above-ground parts of plants, or attack the plants through the soil, and against seed-borne pathogens.

They display a particularly good activity against parasitory fungi on above-ground parts of plants.

As plant-protection agents, the active compounds according to the invention can be used with particularly good success for combating powdery mildew fungi, for example for combating cereal mildew.

It should be emphasized particularly that the active compounds according to the invention not only display a protective action but are also curatively active, that is to say they are active when used after contamination with the spores of the fungus. The systemic action of the compounds should also be pointed out. Thus it is possible to protect plants against fungal attack if the active compound is supplied to the above-ground parts of the plant through the soil and through the root. As plant-protection agents, the compounds according to the invention can be used for the treatment of soil, for the treatment of seed and for the treatment of above-ground parts of plants.

The compounds according to the invention are well tolerated by plants. They have only a low toxicity towards warm-blooded animals and because of their low odor and their good tolerance by human skin they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, bactericides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 1–95% by weight, and preferably 5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to 95% by weight of the active compound or even the 100% active substance alone, e.g. about 20–100% by weight of the active compound.

Especially when used as leaf fungicides, the concentrations of active compound in the ready-to-use forms can be varied within a fairly wide range. They are generally between 0.05 and 0.0001 per cent by weight.

For the treatment of seed, amounts of active compound of 0.01 to 50 g per kilogram of seed, preferably 0.1 to 30 g per kilogram, are generally used.

For the treatment of soil, amounts of active compound of 1 to 1,000 g per cubic meter of soil, preferably of 10 to 200 g per cubic meter, are used.

Furthermore, the present invention contemplates methods of selectively killing, combating or controlling pests, e.g. fungi, which comprises applying to at least one of correspondingly (a) such fungi and (b) the corresponding habitat thereof, i.e. the locus to be protected, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

mildew pustules formed on the leaves over the course of 6 days.

The degree of infection was expressed as a percentage of the infection of the untreated control plants. Thus, 0% denotes no infection and 100% denotes the same degree of infection as in the case of the untreated control. The active compound was the more active, the lower the degree of mildew infection.

The active compounds and concentrations of active compound in the seed-treatment agent, as well as the amount used of the latter, and the percentage infection with mildew can be seen from the table which follows:

Table 1

| Active compounds | Powdery mildew of barley test (*Erysiphe graminis var. hordei*)/systemic | | |
|---|---|---|---|
| | Active compound concentration in the dressing in % by weight | Amount of dressing used in g/kg of seed | Infection in % of the untreated control |
| Without dressing | — | — | 100.0 |
| (Compound 2: CH₃—C(CH₃)₂—CO—CH(CH₂-imidazolyl)—O—C₆H₄—Cl) | 25 / 25 | 10 / 4 | 0.0 / 0.0 |
| (Compound 3: CH₃—C(CH₃)₂—CO—CH(CH₂-imidazolyl)—O—C₆H₃Cl₂) | 25 / 25 | 10 / 4 | 0.0 / 0.0 |
| (B) (known) Zn ethylenebisdithiocarbamate | 30 | 10 | 100.0 |

EXAMPLE 1

Powdery mildew of barley (*Erysiphe graminis var. hordei*)/systemic (fungal disease of cereal shoots)

The active compounds were used as pulverulent seed-treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis var. hordei* and grown further at 21°–22°C and 80–90% relative atmospheric humidity and 16 hours' exposure to light. The typical

EXAMPLE 2

Shoot treatment test/powdery mildew of cereal (leaf-destructive mycosis)

To produce a suitable preparation of active compound, 0.25 g part by weight of active compound was taken up in 25 parts by weight of dimethylformamide and 0.06 part by weight of emulsifier W and thereafter 975 parts by weight of water were added. The concentrate was diluted with water to the desired final concentration of the spray liquor.

To test for protective activity, single-leaved young barley plante of the Amsel variety were sprayed with the preparation of active compound until dew-moist. After drying, the young barley plants were dusted with spores of *Erysiphe graminis var. hordei*.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% means no infection and 100% denotes the same degree of infection as in the case of the untreated control. The active compound was the more active, the lower the degree of rust infection.

The active compounds, active-compound concentrations in the spray liquor and degrees of infection can be seen from the table which follows:

The process of the present invention is illustrated by the following preparative Examples:

EXAMPLE 3 a. The starting material was prepared as follows:

Table 2

| Active compounds | Shoot treatment test/powdery mildew of cereal/protective | | |
|---|---|---|---|
| | | Active compound concentration in the spray liquor in % by weight | Infection in % of the untreated control |
| untreated | | — | 100.0 |
| 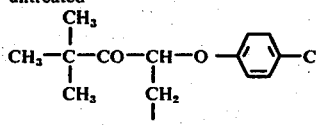 | (2) | 0.025<br>0.01<br>0.001 | 0.0<br>0.0<br>16.3 |
| 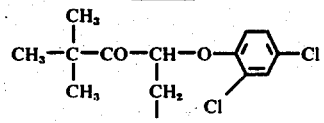 | (3) | 0.025<br>0.01<br>0.001 | 0.0<br>0.0<br>10.0 |
| 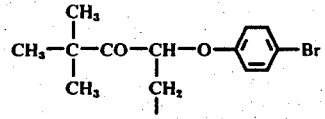 | (4) | 0.01<br>0.001<br>0.0005 | 16.3<br>28.8<br>41.3 |
| 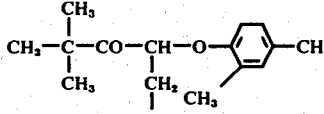 | (6) | 0.01<br>0.001 | 25.0<br>25.0 |
| 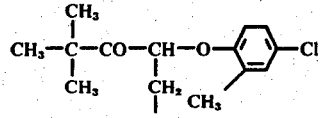 | (9) | 0.01<br>0.001 | 0.0<br>25.0 |
| 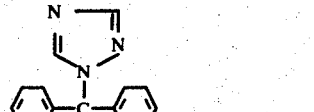 | (known) (A) | 0.01<br>0.001 | 50.0<br>68.8 |
| 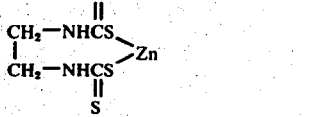 | (known) (B) | 0.025 | 100.0 |

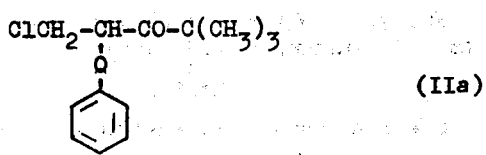

(IIa)

192.2 g (1 mole) of 1-phenoxy-3,3-dimethyl-butan-2-one of boiling point 75°–83°C/0.08 mm Hg, prepared according to U.S. Pat. No. 3,812,142, the disclosure of which is incorporated herein by reference, were dissolved in 800 ml of ethanol and 240 ml (2.4 moles) of 30% strength formaldehyde solution were added thereto, followed by about 50 ml of 10% strength sodium hydroxide solution to give a pH of 9. The reaction mixture was heated for 4 hours under reflux and the solvent was distilled off in vacuo. The resulting precipitate was filtered off, well rinsed with petroleum ether and discarded. The filtrate was freed from the solvent in vacuo. The resulting oil was taken up in ether and extracted by shaking with water. The organic phase was dried over sodium sulfate and then freed from the solvent, and the residue was purified by vacuum distillation.

145 g (65% of theory) of 1-hydroxy-2-phenoxy-4,4-dimethyl-pentan-3-one of boiling point 95°–100°C/0.1 mm Hg were obtained.

111.1 g (0.5 mole) of 1-hydroxy-2-phenoxy-4,4-dimethyl-pentan-3-one were dissolved in 500 ml of methylene chloride. 62 g (0.52 mole) of thionyl chloride were added to this solution at room temperature. The start of the reaction could be accelerated by gentle warming. After two hours' reaction time at room temperature, the solvent was distilled off in vacuo and the oily residue was degassed in a high vacuum.

93.0 g (77% of theory) of 1-chloro-4,4-dimethyl-2-phenoxy-pentan-3-one were obtained as an oil with a refractive index $n_D^{20}$ of 1.5081 and boiling point of 110°C/0.4 mm Hg.

The other starting compounds could be obtained in the same manner.

EXAMPLE 3 b)

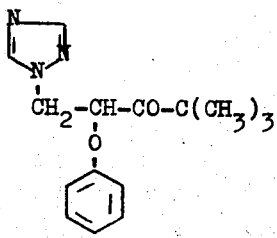

(1)

24 g (0.1 mole) of 1-chloro-4,4-dimethyl-2-phenoxy-pentan-3-one, dissolved in 50 ml of anhydrous acetone, were slowly added dropwise to a suspension of 13.8 g (0.1 mole) of potassium carbonate and 13.8 g (0.2 mole) of 1,2,4-triazole in 400 ml of anhydrous acetone at the boil, while stirring and using a reflux condenser. The reaction was complete after stirring for 17 hours at the boil under reflux.

The precipitate was filtered off after cooling and was well rinsed with anhydrous acetone and discarded. The filtrate was freed from the solvent in vacuo. The oily residue was taken up in methylene chloride and repeatedly extracted by shaking with water. The organic phase was dried over sodium sulfate and the solvent was distilled off in vacuo. The resulting oil crystallized after trituration with pentane.

19.5 g (71% of theory) of 1-(1,2,4-triazolyl-1')-2-phenoxy-4,4-dimethyl-pentan-3-one of melting point 56°–58°C were obtained.

The compounds shown in the table which follows were obtained in the manner described in Example 3.

Table 3

| Compound No. | X | n | Melting point, °C |
|---|---|---|---|
| 2 | 4-Cl | 1 | 55–57 |
| 3 | 2,4-Cl₂ | 2 | 75–77 |
| 4 | 4-Br | 1 | 56–58 |
| 5 | 4-CH₃ | 1 | 42–44 |
| 6 | 2,4-(CH₃)₂ | 2 | 62–64 |
| 7 | 3,4-(CH₃)₂ | 2 | 64–65 |
| 8 | 2,3-(CH₃)₂ | 2 | 47–48.5 |
| 9 | 2-CH₃, 4-Cl | 2 | 63–65 |
| 10 | 2,5-Cl₂ | 2 | 78–79.5 |
| 11 | 3-Cl | 1 | 73.5–74 |
| 12 | 2-Cl | 1 | 67–68.5 |
| 13 | 4-F | 1 | 71–72 |
| 14 | 4-NO₂ | 1 | 97–98 |

Other compounds which can be similarly prepared include:
1-(1,2,4-triazolyl-1')-2-m-trifluoromethylphenoxy-4,4-dimethyl-pentan-3-one,
1-(1,2,4-triazolyl-1')-2-p-chlorodifluoromethyl-phenoxy-4,4-dimethyl-pentan-3-one,
1-(1,2,4-triazolyl-1')-2-o-isopropoxyphenoxy-4,4-dimethyl-pentan-3-one,
1-(1,2,4-triazolyl-1')-2-(3'',5''-dimethyl-4''-n-butylthio-phenoxy)-4,4-dimethyl-pentan-3-one,
1-(1,2,4-triazolyl-1')-2-p-ethylsulfonylphenoxy)-4,4-dimethyl-pentan-3-one,
1-(1,2,4-triazolyl-1')-2-p-cyanophenoxy-4,4-dimethyl-pentan-3-one,
1-(1,2,4-triazolyl-1')-2-p-carbomethoxyphenoxy-4,4-dimethyl-pentan-3-one,
1-(1,2,4-triazolyl-1')-2-p-diphenoxy-4,4-dimethyl-pentan-3-one,
1-(1,2,4-triazolyl-1')-2-pentachlorophenoxy-4,4-dimethyl-pentan-3-one,
1-(1,2,4-triazolyl-1')-2-phenoxy-4,4-dimethyl-pentan-3-oxime,
1-(1,2,4-triazolyl-1')-2-phenoxy-4,4-dimethyl-pentan-3-hydrazone,
1-(1,2,4-triazolyl-1')-2-phenoxy-3,3-dihydroxy-4,4-dimethyl-pentane hydrochloride,
1-(1,2,4-triazolyl-1')-2-phenoxy-3,3-dimethoxy-4,4-dimethyl-pentane,
and the like, and their salts, It will be appreciated that the instant specification and examples are set forth by way of illustration and not limitation, and that various modifications and

What is claimed is:
1. A 1-ethyl-triazole of the formula

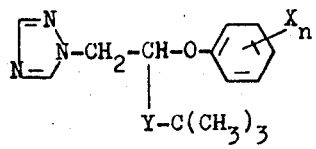

in which
n is an integer from 0 to 3,
X is fluorine, chlorine, bromine, halogenalkyl with 1 or 2 carbon atoms and 2 to 5 halogen atoms, straight-chain or branched alkyl with 1 to 4 carbon atoms, alkyoxy or alkylthio with 1 to 4 carbon atoms, alkylsulfonyl with 1 to 4 carbon atoms or phenyl, and
Y is a keto group or a functional derivative of a keto group selected from ketal groups —C(OR)$_2$— wherein R is hydrogen or an alkyl radical with 1 to 4 carbon atoms, and oxime and hydrazone groups,
or a salt thereof with fungicidal activity.

2. The compound according to claim 1 wherein such compound is 1-(1,2,4-triazolyl-1')-2-p-chlorophenoxy-4,4-dimethyl-pentan-3-one of the formula

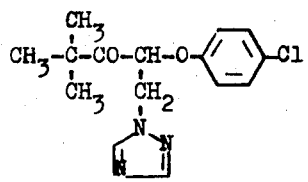

or a salt thereof with fungicidal activity.

3. The compound according to claim 1 wherein such compound is 1-(1,2,4-triazolyl-1')-2-(2'',4''-dichlorophenoxy)4,4-dimethyl-pentan-3-one of the formula

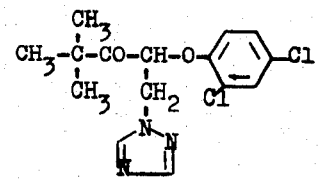

or a salt thereof with fungicidal activity.

4. The compound according to claim 1 wherein such compound is 1-(1,2,4-triazolyl-1')-2-p-bromophenoxy-4,4-dimethyl-pentan-3-one of the formula

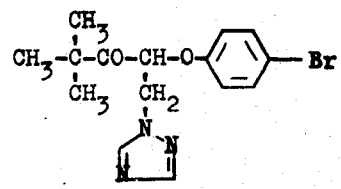

or a salt thereof with fungicidal activity.

5. The compound according to claim 1 wherein such compound is 1-(1,2,4-triazolyl-1')-2-(2''-methyl-4''-chlorophenoxy)-4,4-dimethyl-pentan-3-one of the formula

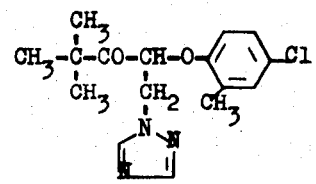

or a salt thereof with fungicidal activity.

6. The compound according to claim 1 wherein such compound is 1-(1,2,4-triazolyl-1')-2-p-fluorophenoxy-4,4-dimethyl-pentan-3-one of the formula

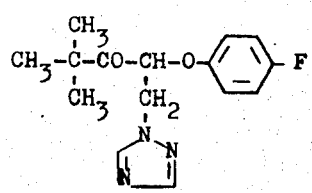

or a salt thereof with fungicidal activity.

* * * * *